US009442282B2

(12) United States Patent
Kuroda et al.

(10) Patent No.: US 9,442,282 B2
(45) Date of Patent: Sep. 13, 2016

(54) ORGANISM SAMPLE OBSERVATION DEVICE

(75) Inventors: Hideo Kuroda, Kawasaki (JP); Hirotada Watanabe, Yokohama (JP); Yoichi Wada, Kawasaki (JP); Yasujiro Kiyota, Tokyo (JP); Ryuji Koshiba, Yokohama (JP); Takayuki Uozumi, Machida (JP)

(73) Assignee: NIKON CORPORATION, Tokyo (JP)

( * ) Notice: Subject to any disclaimer, the term of this patent is extended or adjusted under 35 U.S.C. 154(b) by 1193 days.

(21) Appl. No.: 13/251,673

(22) Filed: Oct. 3, 2011

(65) Prior Publication Data

US 2012/0133755 A1    May 31, 2012

Related U.S. Application Data

(63) Continuation of application No. PCT/JP2010/056421, filed on Apr. 9, 2010.

(30) Foreign Application Priority Data

Apr. 10, 2009  (JP) .............................. P2009-095505

(51) Int. Cl.
   *G02B 21/36* (2006.01)
   *G01N 21/64* (2006.01)
   *G02B 21/16* (2006.01)

(52) U.S. Cl.
   CPC ......... *G02B 21/365* (2013.01); *G01N 21/6486* (2013.01); *G02B 21/16* (2013.01)

(58) Field of Classification Search
   None
   See application file for complete search history.

(56) References Cited

U.S. PATENT DOCUMENTS

| | | | |
|---|---|---|---|
| 7,268,939 B1 * | 9/2007 | McDowell | .................... 359/368 |
| 2007/0058054 A1 | 3/2007 | Kagayama et al. | |
| 2009/0028544 A1 | 1/2009 | Ogihara | |
| 2009/0087177 A1 | 4/2009 | Uchida | |
| 2009/0237502 A1 | 9/2009 | Maiya | |

FOREIGN PATENT DOCUMENTS

| | | |
|---|---|---|
| JP | 2004-309719 | 11/2004 |
| JP | 2008-52227 | 3/2008 |

(Continued)

OTHER PUBLICATIONS

International Search Report for PCT/JP2010/056421, mailed May 18, 2010.

(Continued)

*Primary Examiner* — Geepy Pe

(57) ABSTRACT

A biological specimen observation apparatus whereby observation of a biological specimen can be performed accurately. In macro observation, a biological change region is extracted from a macro image, a micro observation point corresponding to an extracted biological change region is registered, and an object for tracking is identified. In micro observation, it is judged from the micro image whether or not biological change has continued in the biological change region at the micro observation point, and the registered micro observation point is updated on the basis of this judgment result. It is possible to carry out both macro observation for detecting a biological change region and micro observation for observing the progress of growth of a partial minute region where biological change has been exhibited, and to carry out accurate observation of a biological specimen.

10 Claims, 10 Drawing Sheets

(56) References Cited

FOREIGN PATENT DOCUMENTS

| | | |
|---|---|---|
| JP | 2008-58249 | 3/2008 |
| JP | 2008-139487 | 6/2008 |
| JP | 2008-139488 | 6/2008 |
| WO | 2008/068891 A1 | 6/2008 |
| WO | 2009/031476 A1 | 3/2009 |

OTHER PUBLICATIONS

Extended European Search Report mailed Feb. 7, 2013 for corresponding European Application No. 10761751.6.
International Search Report mailed May 18, 2010 issued in corresponding International Patent Application No. PCT/JP2010/056421.

* cited by examiner

ORGANISM SAMPLE OBSERVATION DEVICE

This application is a continuation under 35 USC 111(a) of International Application PCT/JP2010/056421, filed Apr. 9, 2010.

TECHNICAL FIELD

The present invention relates to a biological specimen observation apparatus.

BACKGROUND ART

Conventionally, a biological specimen observation apparatus which carries out observation of the progress of growth of a cultivated biological specimen is known.

In an apparatus of this kind, a method using time lapse observation is generally employed as a method for acquiring observation images of a biological specimen, but the following techniques have been proposed in the prior art, for example.

Patent Document 1 describes technology which enables the start of operation of an automatic time lapse observation when it has been detected that there has been a change in a biological specimen which is an observation object, after which, if it is detected that change in the biological specimen has stopped, the operation of automatic time lapse observation is halted.

Patent Document 1: Japanese Patent Application Publication No. 2004-309719

However, in the case of a technique which is disclosed in Patent Document 1, an image for detecting change in a biological specimen and an image obtained by time lapse observation started after detection are set to the same magnification rate at all times, and therefore it is not possible to observe a region where the biological specimen has changed at a high magnification rate, and hence there is a problem in that the biological specimen cannot be observed accurately.

SUMMARY OF THE INVENTION

The present invention was devised in view of these circumstances, and makes it possible to carry out accurate observation of a biological specimen so as to obtain an observation image at a suitable magnification rate in accordance with the detection circumstances of the biological specimen.

A first biological specimen observation apparatus according to the present invention is a biological specimen observation apparatus which observes temporal change in a biological specimen, having: macro image acquisition means for acquiring a macro image by capturing an image of a macro region of a broad range of the biological specimen, while time lapse observation is performed; biological change region extracting means for extracting a biological change region, which is a region of change in the biological specimen, from the acquired macro image; micro observation point setting means for registering a micro observation point corresponding to the extracted biological change region; micro image acquisition means for capturing an image of a micro region of change in the biological specimen identified at the micro observation point, while time lapse observation is performed; and judgment means for judging whether or not biological change has continued in the biological change region at the micro observation point, from the acquired micro image; wherein the micro observation point setting means updates the registered micro observation point on the basis of a judgment result by the judgment means.

A second biological specimen observation apparatus according to the present invention is a biological specimen observation apparatus which observes temporal change in a biological specimen, having: macro image acquisition means for acquiring a macro image by capturing an image of a macro region of the biological specimen, while time lapse observation is executed; micro observation point setting means for identifying a micro observation point where micro observation is to be performed in the macro region of the biological specimen, on the basis of the macro images of a time series obtained by the macro image acquisition means; and micro image acquisition means for performing time lapse observation and acquiring micro images of the biological specimen at the micro observation point identified by the micro observation point setting means.

A third biological specimen observation apparatus according to the present invention is a biological specimen observation apparatus which observes temporal change in a biological specimen, having: macro image acquisition means for acquiring a macro image by capturing an image of a macro region of a broad range of the biological specimen, while time lapse observation is performed; and micro image acquisition means for acquiring a micro image by capturing an image of a micro region in the macro region of the biological specimen, while time lapse observation is performed; wherein temporal change in the biological specimen is analyzed from the acquired macro image and micro image by the macro image acquisition means and the micro image acquisition means.

According to the present invention, it is possible to carry out observation of a biological specimen accurately.

MODE OF IMPLEMENTING THE INVENTION

Below, an embodiment of the present invention is described with reference to the drawings.

Figure 1:
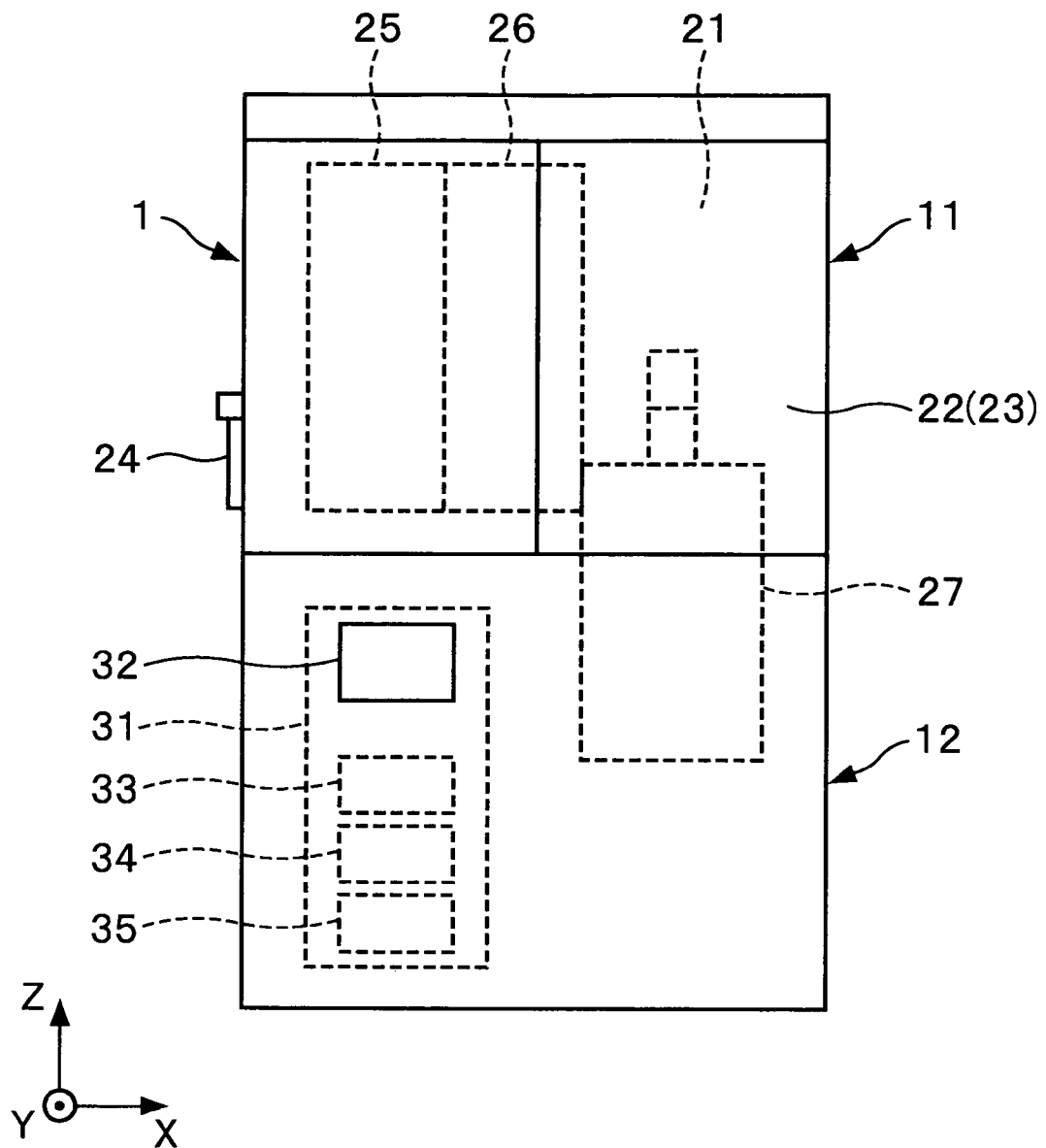
FIG. 1 is a front diagram showing the general composition of a biological specimen observation apparatus to which the present invention is applied.

FIG. 1 is a front view diagram showing the general composition of a biological specimen observation apparatus to which the present invention is applied.

In FIG. 1, the solid lines indicate the structure of parts which are visible in external view, and the broken lines indicate the structure of internal parts which are not visible in external view.

As shown in FIG. 1, the biological specimen observation apparatus 1 includes a first frame 11 in which cultivation of a biological specimen is carried out, and a second frame 12 which constitutes a control apparatus. The first frame 11 is used in a state of being mounted on top of the second frame 12.

A thermostatic chamber 21 which is covered with a heat insulating member is formed inside the first frame 11. This thermostatic chamber 21 is connected to the exterior by means of a front surface opening 23 which is formed on the front surface of the first case 11 (front surface door 22), and an inward and outward conveyance port 24 formed in the left-hand side face as viewed from the front surface of the first case 11.

The thermostatic chamber 21 is provided with, for example, a temperature control mechanism consisting of a temperature adjustment apparatus, or the like, employing a Peltier element, a humidity control mechanism consisting of a spraying apparatus, or the like, which sprays a mist, a gas control mechanism consisting of a gas introduction unit, or the like, which is connected to an external carbon dioxide gas cylinder, an environment sensor which determines the cultivation environment of the biological specimen in the internal space, and the like (all omitted from the drawings). By this means, the interior of the thermostatic chamber 21 is sealed in order to maintain the cultivation environment of the biological specimen during cultivation of the biological specimen, and is kept at a uniform temperature by circulating the air, for example, thereby maintaining the interior of the thermostatic chamber 21 at a temperature of 37° C., a humidity of 90%, and a carbon dioxide concentration of 5%, and so on.

Moreover, a stocker 25, a vessel conveyance mechanism 26 and an observation unit 27 are accommodated inside the thermostatic chamber 21 of the first frame 11.

The stocker 25 is divided in the up/down direction by a plurality of shelves, whereby culture vessels 15 (FIG. 2) can be accommodated horizontally therein.

The vessel conveyance mechanism 26 is provided with a conveyance arm section which supports a holder, and various mechanisms (not illustrated) for conveying culture vessels 15. The vessel conveyance mechanism 26 is able to move a holder supported on the conveyance arm section, in the vertical direction (Z direction) or the horizontal directions (X and Y directions), or to rotate the holder through 180 degrees about the Z axis.

Next, the observation unit 27 is described with reference to FIG. 2.

Figure 2:
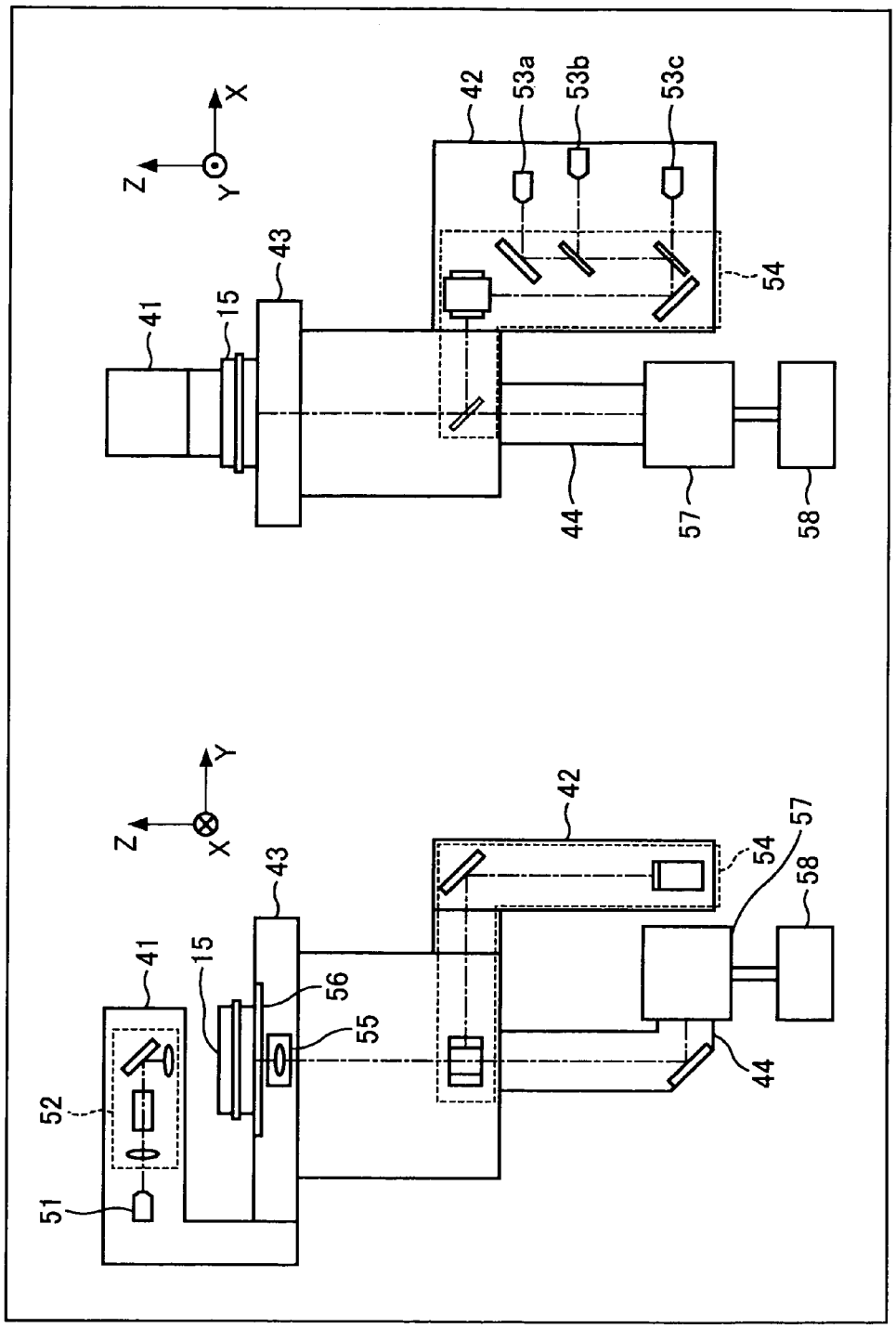
FIG. 2 is a diagram showing a detailed example of the composition of an observation unit.

A front surface diagram of the observation unit 27 is shown on the right-hand side of FIG. 2, and a side face diagram of the observation unit 27 is shown on the left-hand side of FIG. 2.

As shown in FIG. 2, the observation unit 27 is constituted by a transmission light illumination unit 41, an epifluorescent illumination unit 42, a specimen platform 43 and an observation unit 44.

The transmission light illumination unit 41 is formed in an arm shape so as to extend upwards from the side portion of the specimen platform 43 and then extend over the culture vessel 15 which is loaded on the specimen platform 43. A transmission light LED (Light Emitting Diode) 51 and a transmission light optical system 52 are accommodated inside the transmission light illumination unit 41. The transmission light LED 51 emits light of a prescribed wavelength region. The light from the transmission light LED 51 is irradiated from the upper side onto a culture vessel 15 which is loaded on the specimen platform 43, via the transmission light optical system 52.

The epifluorescent illumination unit 42 is constituted by fluorescence LEDs 53a to 53c, and a fluorescence optical system 54. The fluorescence LEDs 53a to 53c (simply called "fluorescence LEDs 53" below) respectively emit light of different wavelengths, in other words, light of a prescribed wavelength (excitation light) corresponding to fluorescent material in the biological specimen in the culture vessel 15 is emitted. The excitation light from the transmission light LED 53 is irradiated from the lower side onto a culture vessel 15 which is loaded on the specimen platform 43, via a fluorescent light optical system 54 and an object lens 55.

The specimen platform 43 is made of a light transmitting material and light from the transmission light illumination unit 41 and light from the fluorescent material included in the biological specimen which is excited by the light from the epifluorescent illumination unit 42 in introduced into the observation unit 44. Furthermore, an object lens 55 which condenses light introduced to the observation unit 44, and a stage 56 which moves a culture vessel 15 in the vertical direction or the horizontal direction in order to capture an image of a prescribed location of the biological specimen, and the like, are also provided on the specimen platform 43. The object lens 55 is constituted by a plurality of object lenses having different magnification rates (for example, 2×, 4×, 10×, 20×, 40×, . . . , etc.), and hence the observation magnification rate can be switched appropriately in accordance with the observation circumstances.

The observation unit 44 is constituted by an imaging unit 57 and an image processing unit 58. The imaging unit 57 has an imaging element, such as a CCD (Charge Coupled Device), or the like. On an image surface of the CCD, an image produced by the light from the transmission light irradiation unit 41 and an image produced by light from the fluorescent material contained in the biological specimen which is excited by light from the epifluorescent illumination unit 42 are formed by an image forming optical system.

The image processing unit 58 obtains image data represented by a digital signal, by applying analog signal processing for amplifying the analog image signal from the imaging unit 57, for example, and then converting the signal from analog to digital (A/D).

Returning to FIG. 1, besides a portion of the observation unit 27 described above, a control unit 31 is also accommodated inside the second frame 12 on which the first frame 11 is mounted.

The control unit 31 controls the operation of the respective units of the biological specimen observation apparatus 1. More specifically, the control unit 31 executes adjustment of the environmental conditions inside the thermostatic chamber 21, inward and outward conveyance of the culture vessel 15 into and out from the thermostatic chamber 21, observation of the biological specimen inside the culture vessel 15, conveyance of a culture vessel 15 inside the thermostatic chamber 21, and the like, in accordance with an observation schedule or direct instructions based on operations performed by a user.

The observation schedule can be set, for example, by means of a setup screen which is displayed on a display panel 32 which displays various information processed by the control unit 31, and is input by input means, such as a keyboard, or the like, which is connected to the control unit 31. By this means, the observation position, the observation magnification rate, the imaging schedule, and the like, are set up for each sample.

Furthermore, an observation information memory unit 33 is provided inside the control unit 31, and this observation information memory unit 33 stores and accumulates image data corresponding to observation images obtained by time lapse observation which are supplied from the image processing unit 58. The image data stored in the observation information memory unit 33 is recorded in association with identification information for the culture vessel 15 and index information indicating the date and time of image capture. Furthermore, information of various types relating to the observation of the biological specimen, and a history of change in the environmental conditions (temperature, humidity, carbon dioxide concentration, etc.) inside the thermostatic chamber 21, can also be recorded in the observation information memory unit 33.

The image analysis unit 34 carries out image analysis by performing prescribed image analysis processing on the image data accumulated in the observation information memory unit 33. The image analysis unit 34 supplies the image analysis results to the observation control unit 35.

The observation control unit 35 controls the operation of the observation unit 27 in accordance with the observation schedule or direct instructions based on operations performed by a user. Furthermore, the observation control unit 35 controls the operation of the observation unit 27 which carries out observation of a biological specimen in a culture vessel 15, on the basis of the image analysis results from the image analysis unit 34.

The control unit 31 comprises communications means (not illustrated) which are compliant with a prescribed wireless or wired communications standard, and is able to send and receive data to and from external devices, such as a personal computer, via a network. By this means, it is also possible to observe a biological specimen, change the imaging conditions setup, and check the environment in the thermostatic chamber 21 and the observation images, from a personal computer which is positioned in a remote location, using a network.

Furthermore, in the biological specimen observation apparatus 1, observation of two patterns, namely, macro observation and micro observation, are carried out as observation by time lapse.

Here, macro observation means observation using an object lens having a low magnification rate (for example, 2×, 4×) which can obtain an observation image corresponding to a broad region on the biological specimen, as the object lens 55. Below, an observation image obtained by macro observation is called a macro image. Furthermore, micro observation is observation using an object lens having a higher magnification rate than macro observation (for example, 4×, 10×, 20×, 40×). Below, an observation image obtained by micro observation is called a micro image.

In other words, in the observation unit 27, when observation of a broad range of the biological specimen is to be carried out, then an object lens of low magnification rate, from the plurality of object lenses 55, is arranged in the optical path of the light of the biological specimen in the culture vessel 15, and macro observation is carried out. On the other hand, when observation of a particular range of the biological specimen is to be carried out, then an object lens of high magnification rate, from the plurality of object lenses 55, is arranged in the optical path of the light of the biological specimen in the culture vessel 15, and micro observation is carried out. By carrying out macro observation and micro observation, macro images and micro images having different observation magnification rates are accumulated as observation images in the observation information memory unit 33.

Next, the operation of the biological specimen observation apparatus 1 which carries out macro observation and micro observation will be described.

Figure 3:
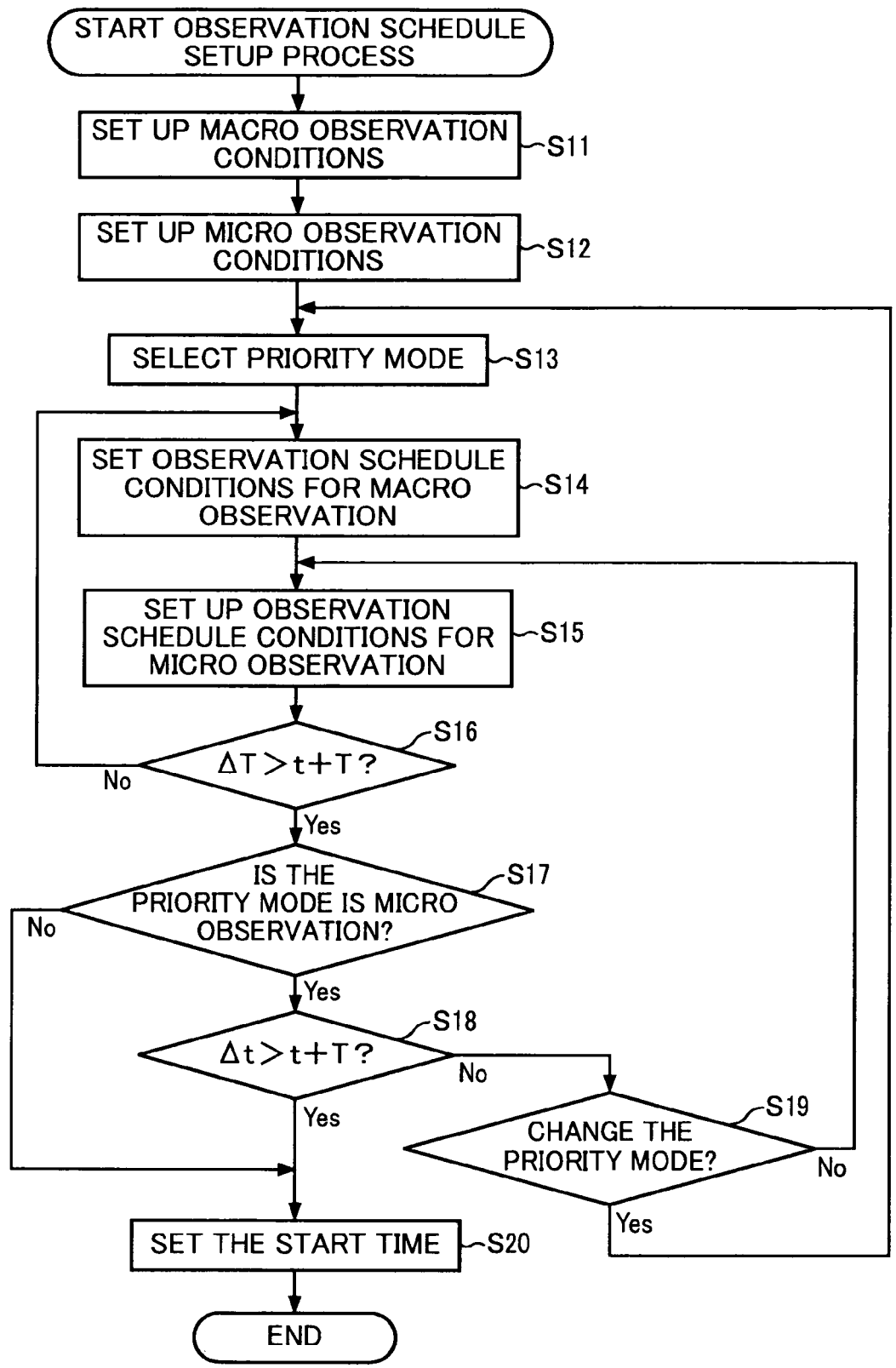
FIG. 3 is a flowchart which describes an observation schedule setting process.

As described above, in the biological specimen observation apparatus 1, observation of temporal change in a biological specimen which is being cultivated is carried out in accordance with an observation schedule, and this observation schedule is set by an operation performed by the user. Therefore, firstly, a process for setting up an observation schedule for macro observation and micro observation will be described with reference to the flowchart in FIG. 3.

This setup process is executed, for example, by the control unit 31, in accordance with an input operation by the user made to a setup screen for setting up observation schedules of various types which is displayed on the display panel 32.

In step S11, when information relating to the observation magnification rate for macro observation and settings for fluorescent observation has been input, the macro observation condition settings are implemented on the basis of these parameters. The observation magnification rate is set, for example, to two times or four times, or the like. Furthermore, in the present embodiment, a case where fluorescent observation is carried out is described, but when fluorescent observation is not carried out, there is not need to set information relating to the settings for fluorescent observation, and only the observation magnification rate is set.

By means of these parameters, the time required for one macro observation (called the macro observation prescribed time T) is determined.

In step S12, when information relating to the observation-magnification rate for micro observation and settings relating to fluorescent observation, the number of frames, and the maximum number of observation points, has been input, the micro observation condition settings are implemented on the basis of these parameters. The observation magnification rate is set, for example, to 10 times or 20 times, or the like. In other words, as described above, the observation magnification rate in micro observation is set so as to be a higher magnification rate than the observation magnification rate for macro observation.

Furthermore, the frame number set as the micro observation condition is the number of micro images acquired within a prescribed time period. If the number of frames is set to a large number, then the data volume of the acquired micro images becomes larger, but since the number of micro images acquired per unit time increases, then it is possible to carry out more detailed micro observation. Furthermore, the maximum number of observation points is the maximum number of positions which can be set for observation as a region where there is change in the biological specimen, in a micro image (hereinafter, called micro observation points). By setting this maximum number to a large number, it is possible to observe change in the biological specimen at a greater number of points. Furthermore, although the micro observation prescribed time t, which is described below, cannot be determined until the number of observation points is designated, the number of observation points is determined on the basis of biological change regions which are extracted from a macro image, and therefore cannot be determined at this stage. Therefore, the micro observation prescribed time t is determined by using this maximum number of observation points. In this way, these two parameters are parameters which are specific to micro observation and therefore do not have to be set as macro observation conditions.

By means of these parameters, the time required for one micro observation operation (called the micro observation prescribed time t) is determined.

In step S13, when information is input indicating which of macro observation and micro observation is prioritized, then priority mode selection is implemented. The subsequent processing is different, depending on which type of observation is prioritized and corresponding details of this are described below.

In step S14, when information has been input in relation to the interval between the nth macro observation and the n+1th macro observation (hereinafter, interval period $\Delta T$) and the number of macro images (number of observations) which can be obtained during the observation period of macro observation, then an observation schedule condition setup for macro observation is implemented on the basis of these parameters. The value of $\Delta T$ is set so as to be a longer interval than the macro observation prescribed time T. In other words, $\Delta T$ is set so as to satisfy the relationship in Formula (1) below.

$$\Delta T > T \quad (1)$$

In step S15, when information is input in relation to the interval between the mth micro observation and the m+1th micro observation (called the interval period $\Delta t$), then setup of the observation schedule conditions for micro observation is implemented on the basis of this parameter. Similarly to Formula (1) relating to $\Delta T$ described above, $\Delta t$ is set so as to be a longer interval than the micro observation prescribed time t, and is set so as to satisfy the relationship in Formula (2) below.

$$\Delta t > t \quad (2)$$

In step S16, satisfying the relationship $\Delta T > t + T$ means a condition for performing micro observation after macro observation, and therefore it is judged whether or not this condition is satisfied. Consequently, in step S16, if it is judged that the relationship $\Delta T > t + T$ is not satisfied, then the procedure returns to step S14, and the values of $\Delta T$, T and t which were described above are reset. On the other hand, if it is judged that the relationship $\Delta T > t + T$ is satisfied, then the processing advances to step S17.

At step S17, it is judged whether or not the priority mode selected in the processing step S13 is micro observation mode. If it is judged in step S17 that macro observation is prioritized, then it is judged that the condition for carrying out micro observation after macro observation is satisfied, ("Yes" at step S16), and the processing then advances to the setup process in step S20. On the other hand, if it is judged that the micro observation is prioritized, then the processing advances to step S18.

In step S18, satisfying the relationship $\Delta t > t + T$ means a condition for performing macro observation after micro observation, and therefore it is judged whether or not this condition is satisfied. Consequently, if it is judged at step S18 that the relationship $\Delta t > t + T$ is satisfied, then it is judged that micro observation is prioritized ("Yes" at step S17), and the processing advances to the setup process in step S20. On the other hand, if it is judged that the relationship $\Delta t > t + T$ is not satisfied, then the processing advances to step S19.

At step S19, it is judged whether or not to change the priority mode in accordance with input operations by the user, and at step S19, if it is judged that the priority mode is changed, then the processing returns to step S13, and a reselection process for the priority mode is carried out. On the other hand, if it is judged at step S19 that the priority mode is not to be changed, then the processing returns to step S15, the observation schedule condition setup for micro observation is carried out again, and the values of T, $\Delta t$ and t described above are reset.

Thereafter, if the judgment in step S17 is "No" or the judgment in step S18 is "Yes", then the processing advances to step S20.

In step S20, when information relating to the start timing of time lapse observation is input, the observation start time is set and the observation schedule is established. Even though an observation schedule has been established, the processing which is executed differs between a case where micro observation has been selected and a case where macro observation has been selected, and therefore the processing which is executed in each type of observation depending on the priority mode will be described individually here while referring to FIG. 4 and FIG. 5.

Figure 4:
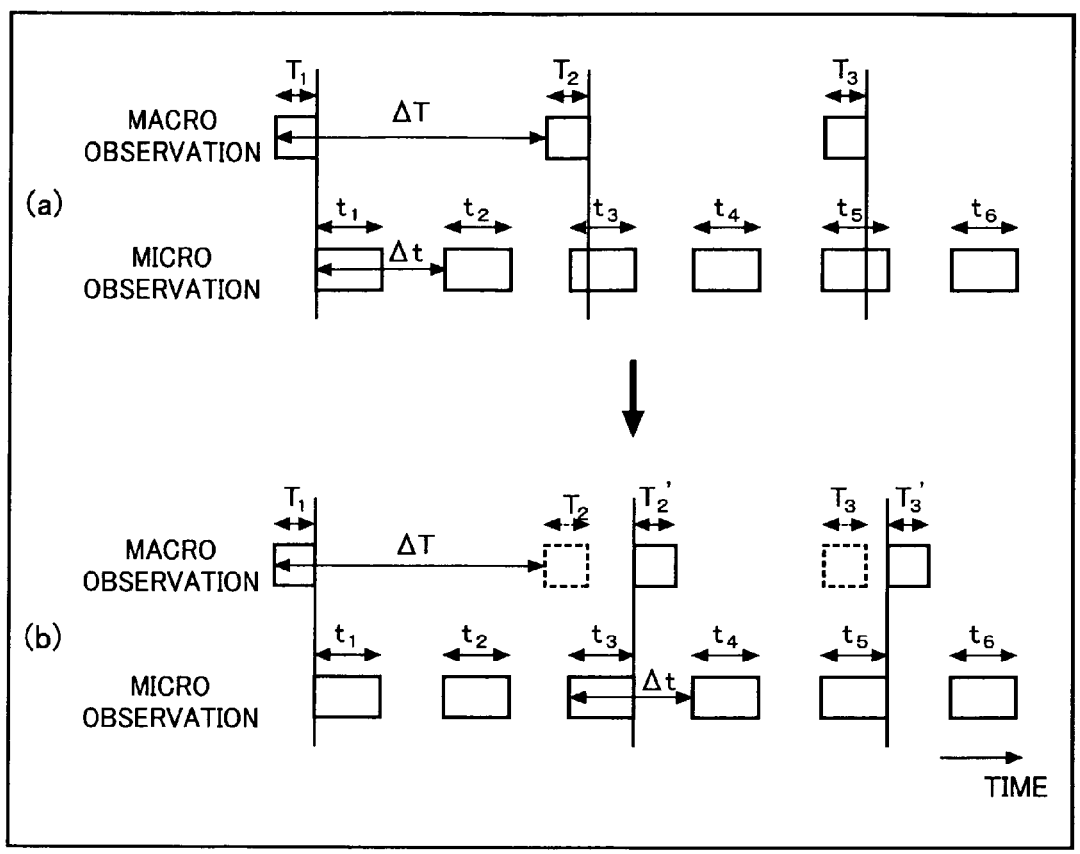
FIG. 4 is a diagram which describes a schedule setting process in the case where the priority mode is set to micro observation.
Figure 5:
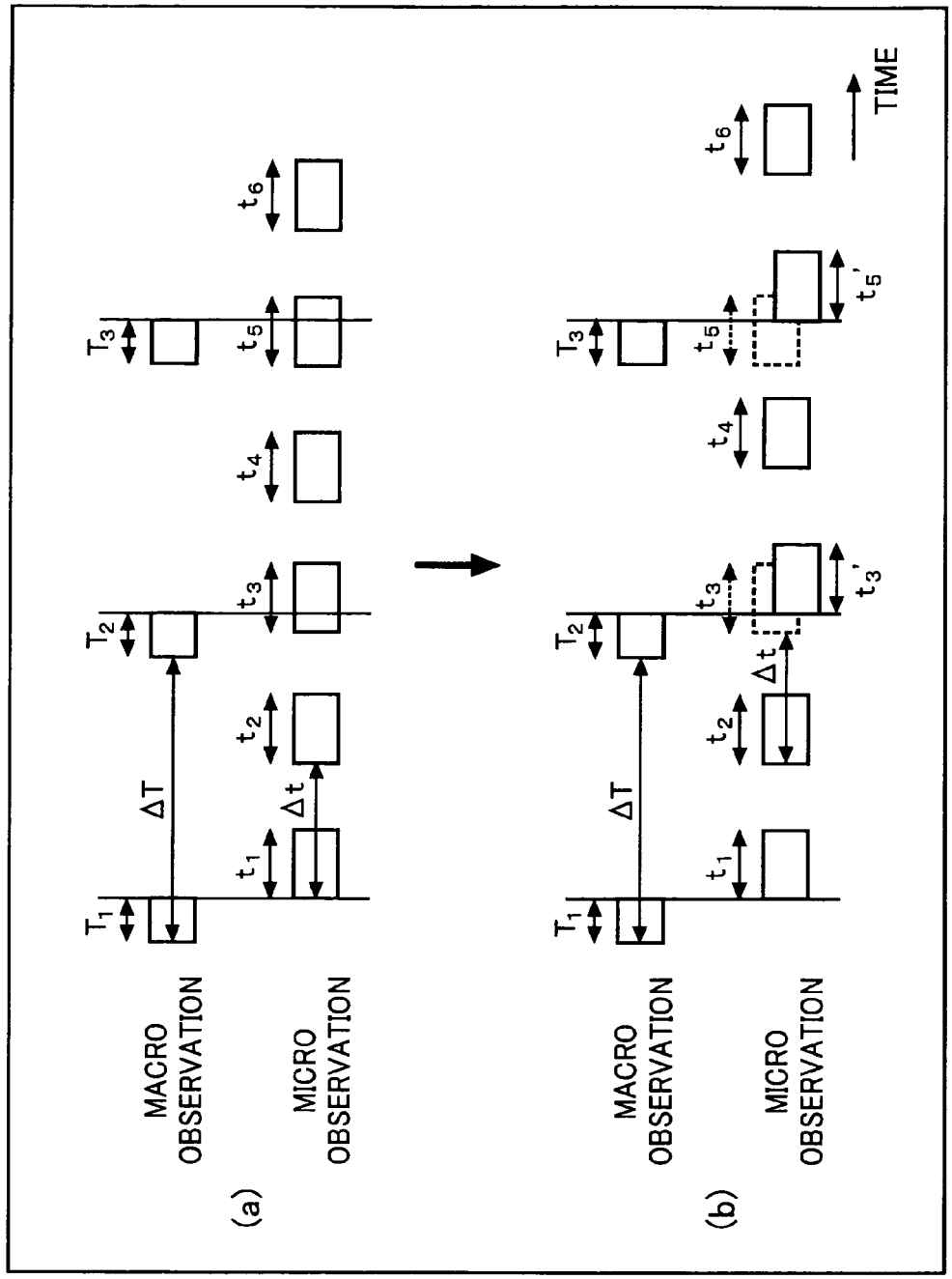
FIG. 5 is a diagram which describes a schedule setting process in the case where the priority mode is set to macro observation.

Firstly, processing in a case where micro observation is selected as the priority mode is described with reference to FIG. 4. In FIG. 4 and FIG. 5, the upper part of the diagram shows an observation schedule of macro observation which is registered in the setup process in step S20, and macro observation requiring observation times of $T_1, T_2, T_3, \ldots, T_n$ is carried out at intervals of $\Delta T$. Furthermore, the lower part of each diagram similarly shows an observation schedule for micro observation which is registered in the setup processing in step S20, and micro observation requiring observation times of $t_1, t_2, t_3, \ldots, t_m$ is carried out at intervals of $\Delta t$.

In the observation schedule in FIG. 4A, micro observation is prioritized, and therefore the relationship $\Delta t > t + T$ is satisfied, but there is overlap between the macro observation time $T_2$ in the upper part and the micro observation time $t_3$ in the lower part and therefore it is not possible to carry out both types of observation in this state. In this case, the macro observation time $T_2$ in the upper part is staggered to a macro observation time $T_2'$ as shown in the observation schedule in FIG. 4B, so as to delay the start time of macro observation. By this means, micro observation at micro observation time $t_3$ is carried out preferentially, and when this micro observation has ended, macro observation is carried out immediately at macro observation time $T_2'$.

In other words, when micro observation is prioritized, $\Delta t$ is uniform, and therefore $\Delta T$ is changed to alter the observation schedule in such a manner that macro observation is carried out after the end of micro observation, as shown by FIG. 4B.

Next, processing in a case where macro observation is selected as the priority mode is described with reference to FIG. 5.

In the observation schedule in FIG. 5A, macro observation is prioritized, and therefore the relationship $\Delta T > t + T$ is satisfied, but similarly to FIG. 4A, there is an overlap between the macro observation time $T_2$ in the upper part and the micro observation time $t_3$ in the lower part. In this case, as indicated by the dotted line in FIG. 5B, the micro observation time $t_3$ in the lower part which overlaps with the macro observation time $T_2$ in the upper part is erased, and macro observation at the macro observation time $T_2$ is carried out preferentially, without carrying out micro observation at micro observation time $t_3$. Furthermore, rather than omitting the micro observation which has an overlapping observation time, by staggering the micro observation time $t_3$ of the lower part to micro observation time $t_3'$ so as to delay the start time of micro observation, it is possible to carry out micro observation at the micro observation time $t_3'$ immediately after the macro observation at macro observation time $T_2$ has ended.

In other words, when macro observation is prioritized, $\Delta T$ is uniform, and therefore $\Delta t$ is changed to alter the observation schedule in such a manner that micro observation is carried out after the end of macro observation, as shown by FIG. 5B.

As described above, a setup process for an observation schedule based on respective priority modes is carried out in step S20 and processing then terminates.

There follows a description of processing for macro observation and micro observation based on time lapse observation which is carried out in accordance with the observation schedule described above, with reference to the flowchart in FIG. 6.

At step S31, the observation unit 27 carries out macro observation of the biological specimen in accordance with control by the observation control unit 35 based on the observation schedule. The macro images obtained by macro observation are accumulated in the observation information memory unit 33.

At step S32, the image analysis unit 34 extracts a region of change in the biological specimen (hereinafter, called a "biological change region") by applying prescribed image analysis processing to the macro images accumulated in the observation information memory unit 33. For example, a macro image which is a fluorescent image is obtained by carrying out fluorescent observation in the observation unit 27, but this macro image includes a luminous point originating from the fluorescence color included in the biological specimen, and this luminous point is extracted by means of a suitable threshold value by image analysis processing. For example, change in the biological specimen, such as formation of a colony, deformation of cells or occurrence of fluorescence, or the like, appears as change in the luminous point of the macro images which are obtained over time by time lapse observation (for example, change in the value (RGB value) of pixels (pixels of interest) at the same position respectively in the n–1th macro image (the macro image at macro observation time $T_{n-1}$) and the nth macro image (the macro image at macro observation time $T_n$)), and therefore the region where this change has occurred is extracted as a biological change region and is supplied to the observation control unit 35.

At step S33, if the biological change region is a newly extracted biological change region, of the biological change regions extracted from the macro images, then the observation control unit 35 newly registers a micro observation point which specifies the central coordinates of the biological change region (for example, the XYZ coordinates of the stage 56 or the object lens 55), whereas if the biological change region is an already registered biological change region, then the observation control unit 35 sets a micro observation point by updating the micro observation point which specifies that biological change region. The information (XYZ coordinates) relating to this micro observation point is stored and set in the observation information memory unit 33, for instance.

In step S34, the observation control unit 35 judges whether or not there is a micro observation point, on the basis of the coordinates of the established micro observation point.

In step S34, if a biological change region has not been extracted and it is judged that there does not exist even one micro observation point, then at step S35, the observation control unit 35 judges whether or not the observation end time has been reached, on the basis of the observation schedule. If it is judged at step S35 that the observation end time has been reached, then the time lapse observation process is terminated. On the other hand, if it is judged at step S35 that the observation end time has not been reached, then at step S36, the observation control unit 35 keeps the observation unit 27 waiting until the next macro observation start time. In this case, it is also possible to receive the input of registration or change of coordinates of the micro observation point in accordance with operations performed by the user; for example, it is possible to set a desired region which has not been extracted in the image analysis processing described above, as a micro observation point.

Thereupon, at step S36, when the macro observation start time is reached, the processing returns to step S31 and the macro observation processing in steps S31 to S36 described above is repeated either until it is judged that there exists a micro observation point or until it is judged that the observation end time has been reached.

If it is judged at step S34 that there is a micro observation point, then at step S37, the observation control unit 35 refers to the information relating to micro observation points stored in the observation information memory unit 33 and judges whether or not there has been an increase or decrease in the number of micro observation points.

If it is judged in step S37 that there has been an increase or decrease in the number of micro observation points, then at step S38, the observation control unit 35 carries out updating of the observation schedule for micro observation, and information relating to the micro observation points which have been increased or decreased is reflected in the observation information memory unit 33. By this means, micro observation is carried out at newly found micro observation points.

On the other hand, if it is judged at step S37 that there has been no increase or decrease in the micro observation points, then there is no need to update the observation schedule for micro observation, and therefore the step S38 is skipped and processing advances to step S39.

At step S39, the observation control unit 35 causes the observation unit 27 to wait until the micro observation start time is reached. In this case, in the observation unit 27, preparatory operations for micro observation of the micro observation points are carried out, such as an operation for switching from an object lens of low magnification rate for macro observation to an object lens of high magnification rate for micro observation, or an operation by the stage 56 for moving the culture vessel 15 in the vertical direction or horizontal direction for the purposes of time lapse observation of the micro observation points, for instance. Furthermore, in this case, it is possible to receive input of the registration or change of a micro observation point in accordance with operations by the user, and to set a new micro observation point.

Thereupon, when the micro observation start time is reached in step S39, then at step S40, the observation unit 27 carries out micro observation of the micro observation point under the control of the observation control unit 35 based on the observation schedule. The micro images obtained by micro observation are accumulated in the observation information memory unit 33.

These micro images are images obtained by microscopic observation of a portion of a macro image in which the whole of the biological specimen can be observed over a broad range, and correspond to a partial minute region of a biological change region which has been extracted by macro observation. In other words, a micro image enables observation of finer changes in a partial minute region of the biological specimen, compared to a macro image, and therefore the biological specimen can be observed in an accurate fashion.

In step S41, the image analysis unit 34 carries out prescribed image analysis processing on the micro images accumulated in the observation information memory unit 33, and judges whether change in the biological specimen has occurred continuously at the micro observation point specified by the processing in step S33, or whether there has been no change.

In step S42, the observation control unit 35 updates the registered micro observation points in accordance with the state of change in the biological change regions at the micro observation points.

More specifically, if it is judged that there is a biological change, then the coordinates of the micro observation points registered (updated) by the macro observation continue to be updated in micro observation as well. In other words, in micro observation, the details of the aspect of the biological specimen after change are tracked by means of high-definition micro images which are identified by micro observation points which have been detected by macro observation.

Furthermore, conversely, if it is judged that there is no biological change, then the observation control unit 35 removes the micro observation point where tracking does not need to be continued, and the acquisition of micro images at this micro observation point is halted. For example, if a colony which is registered as a micro observation point does not satisfy a prescribed standard value based on prescribed image analysis processing and has not been judged to be an iPS colony, then this point is removed from the micro observation points. By suspending observation at points such as this, it is possible to avoid unnecessary processing in the time lapse observation process.

In step S43, the observation control unit 35 judges whether or not the observation end time has been reached, on the basis of the observation schedule. If it is judged at step S43 that the observation end time has been reached, then the time lapse observation process is terminated. On the other hand, if it is judged at step S43 that the observation end time has not been reached, then at step S44, the observation control unit 35 judges whether or not either the next macro observation start time or the next micro observation start time is near, on the basis of the observation schedule.

At step S44, if the next micro observation start time is first, then the procedure returns to step S39, and the micro observation processing in steps S39 to S44 described above is repeated until either it is judged that the next macro observation start time is first or it is judged that the observation end time has been reached. Furthermore, in this case, if a plurality of micro observation points are set and registered, then similar micro observation is carried out for the other micro observation points as well.

On the other hand, if it is judged at step S44 that the next macro observation start time is first, then the procedure returns to step S36. If the macro observation start time has been reached, then the processing returns to step S31, detection of a biological change region is carried out over a broad range as macro observation processing, and the registration and update setting processes for the micro observation points described above are carried out again.

As stated previously, it is possible to carry out both macro observation for detecting a biological change region and micro observation for observing the progress of growth of a partial minute region where biological change has been observed, and therefore it is possible to detect biological change over a broad region, as well as being able to perform detailed observation of a minute region which has changed.

In this way, in the biological specimen observation apparatus 1, it is possible to carry out time lapse observation based on a priority mode which is suited to the objectives of the sample observation.

A macro image which is captured by time lapse observation in macro observation does not have to be captured in one instant, but may be an image produced by pasting together a plurality of captured images using a so-called tiling technique, (hereinafter, called a "tiled image").

Next, the process of extracting a biological change region from a tiled image is described with reference to the flowchart in FIG. 7.

Figure 6:
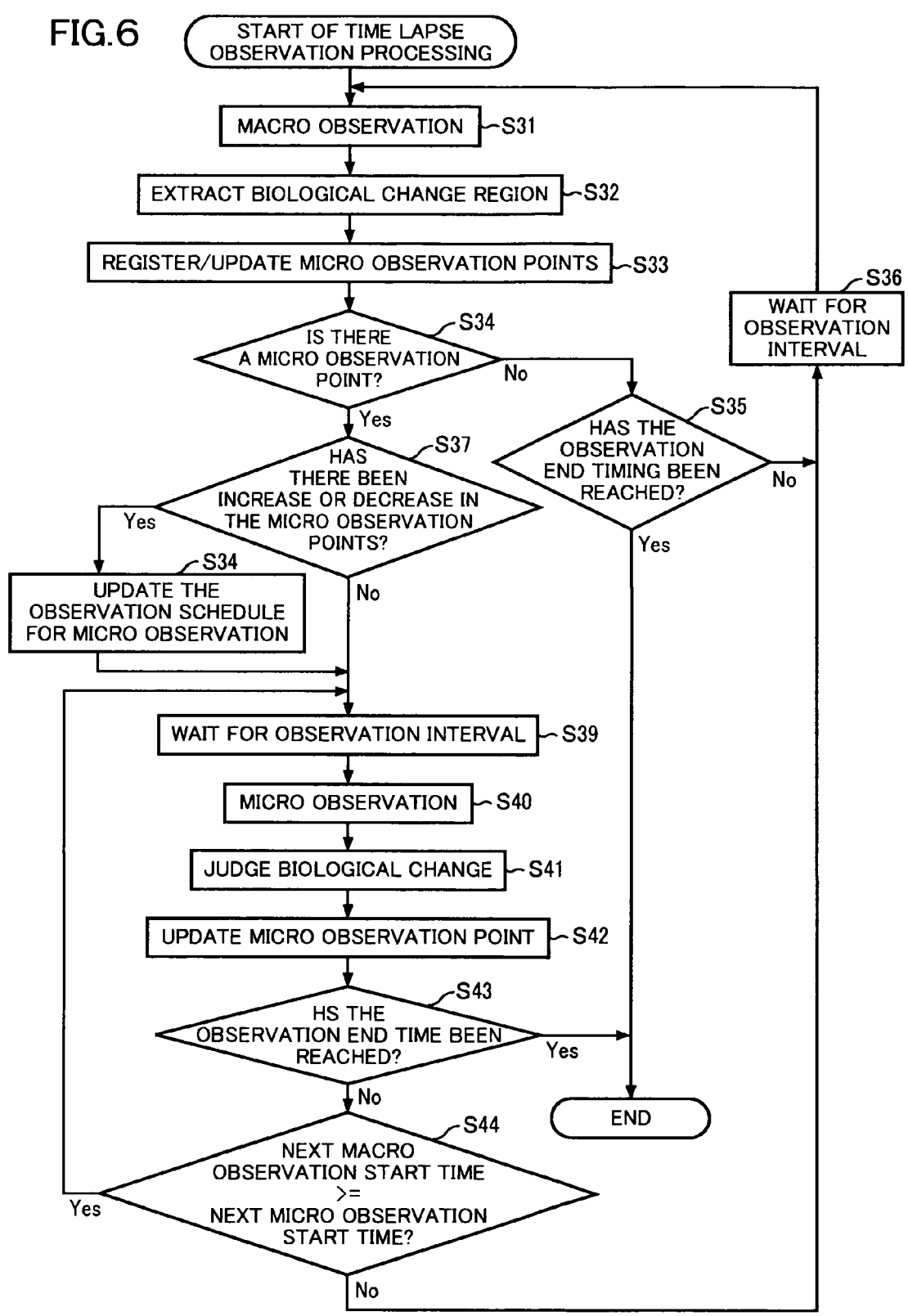
FIG. 6 is a flowchart describing a time lapse observation process.
Figure 7:
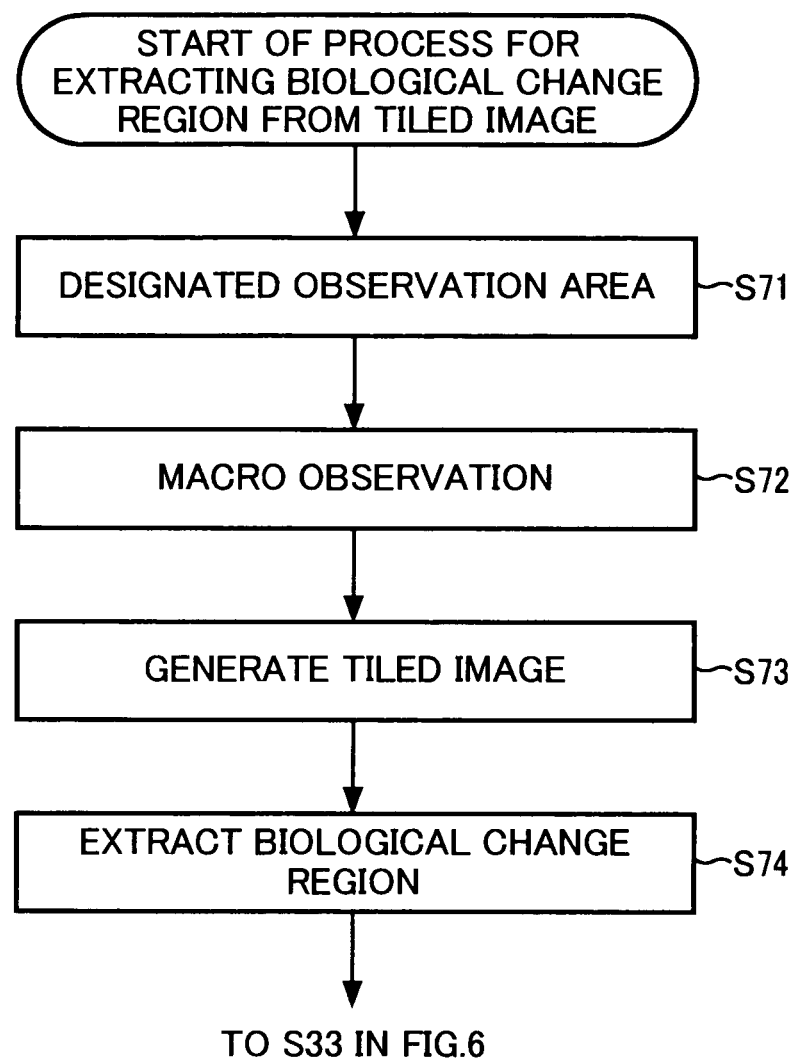
FIG. 7 is a flowchart describing a process for extracting a biological change region from a tiling image.

More specifically, steps S71 to S74 in FIG. 7 correspond to macro observation processing which is executed in steps S31 and S32 in FIG. 6, and the processing from step S74 onwards is similar to the processing in step S33 onwards in FIG. 6.

In step S71, the observation control unit 35 specifies a number of images which are to be acquired from a designated observation area, when a region to be observed by macro observation (observation area) has been designated by an operation performed by the user.

Figure 8:
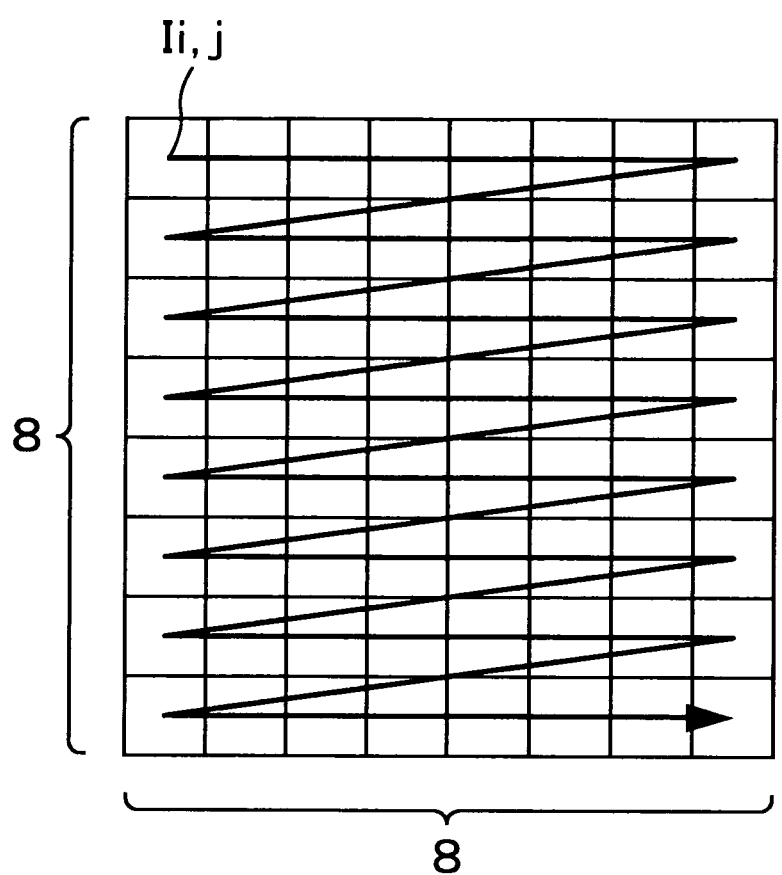
FIG. 8 is a diagram describing tiled image generating means.

At step S72, the observation unit 27 carries out macro observation of the biological specimen in accordance with control by the observation control unit 35. In this macro observation, if an acquired image is represented as captured image $I_{i,j}$ (i: number of scans in the vertical direction; j: number of scans in the horizontal direction), then as shown in FIG. 8, eight captured images $I_{11}$ to $I_{18}$ are acquired by the first scan in the horizontal direction. Thereafter, by performing scanning which includes eight repetitions of a shift operation in the vertical direction, in such a manner that the captured images do not overlap (alternatively, it also possible to adopt a pasting region for pasting together with other captured images which are adjacent in the lateral or longitudinal directions), captured images $I_{21}$ to $I_{28}$, captured images $I_{31}$ to $I_{38}$, . . . , and captured images $I_{81}$ to $I_{88}$, are acquired sequentially, and 8×8 captured images $I_{i,j}$ in FIG. 8 are obtained corresponding to the designated observation area.

In step S73, the image processing unit 58 generates one tiled image from the 8×8 captured images in FIG. 8, for instance, by tiling together the captured images $I_{i,j}$ obtained by scanning. This tiled image corresponds to the macro image shown in FIG. 6.

In step S74, similarly to step S32 in FIG. 6, a biological change region is extracted from the tiling image forming a macro image, by the image analysis unit 34, and thereafter processing similar to that in step S33 in FIG. 6 is carried out.

In this way, even in cases where a image covering a broad region cannot be obtained instantaneously, by tiling a plurality of images to form a prescribed size, it is possible to obtain an image for a broad region, which can be used as a macro image.

In micro observation, an image of a biological change region extracted by macro observation is acquired, but there may be cases where one micro image obtained from a registered micro observation point only includes a portion of a biological change region. In micro observation in cases such as this, it is not possible to obtain an image of the whole of the biological change region, and hence there is a possibility that the biological specimen cannot be observed accurately. Therefore, in the present embodiment, if the whole of a biological change region is not contained completely within one micro image, then an image of the whole region is obtained by combining together images obtained from a peripheral area of a micro observation point (called peripheral images below).

Figure 9:
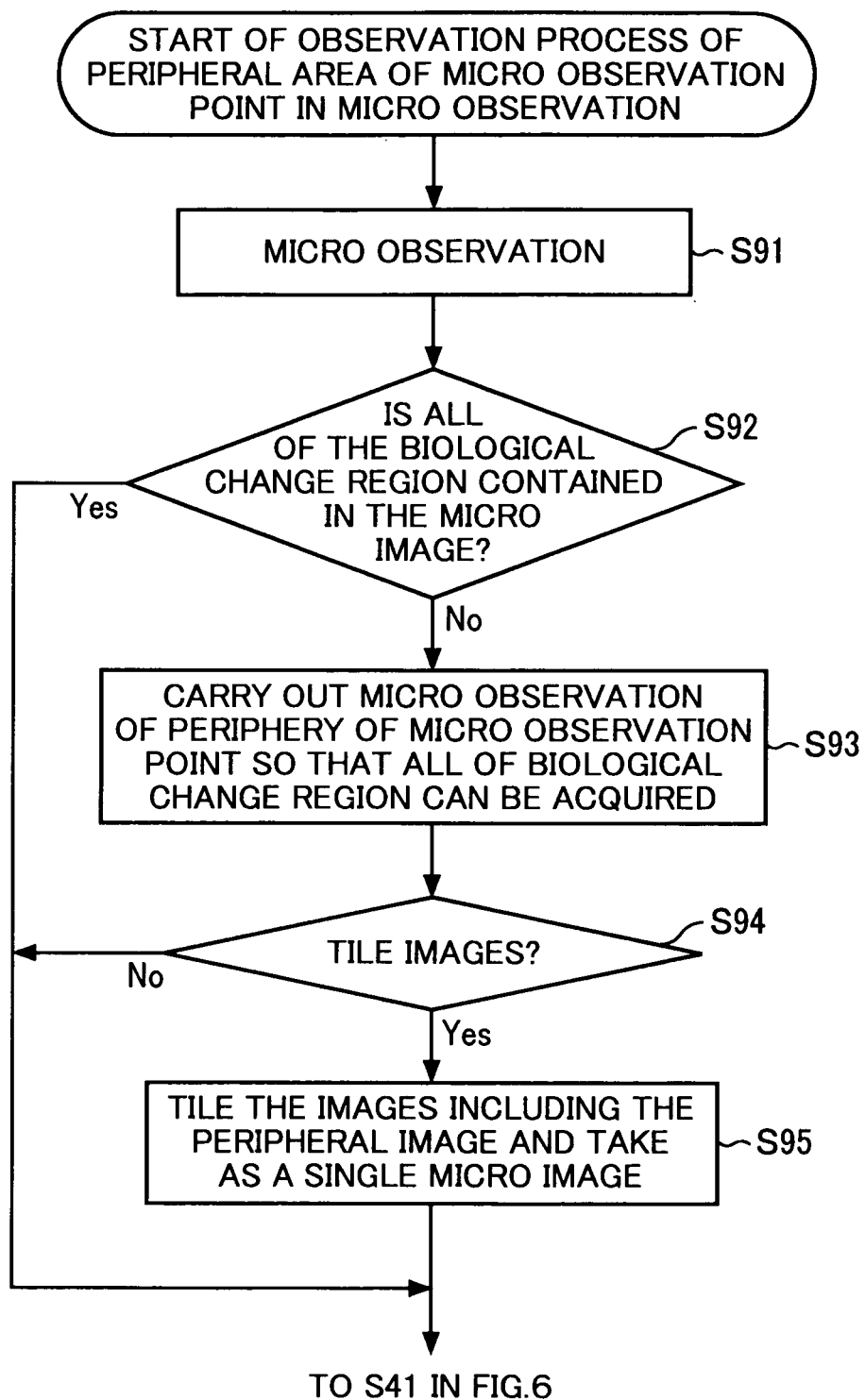
FIG. 9 is a flowchart describing an observation process of a peripheral area of a micro observation point in micro observation.

FIG. 9 is a flowchart describing an observation process of a peripheral area of a micro observation point.

More specifically, steps S91 to S95 in FIG. 9 correspond to micro observation processing which is executed in step S40 in FIG. 6, and the processing from step S95 onwards is similar to the processing in step S41 onwards in FIG. 6.

Figure 10:
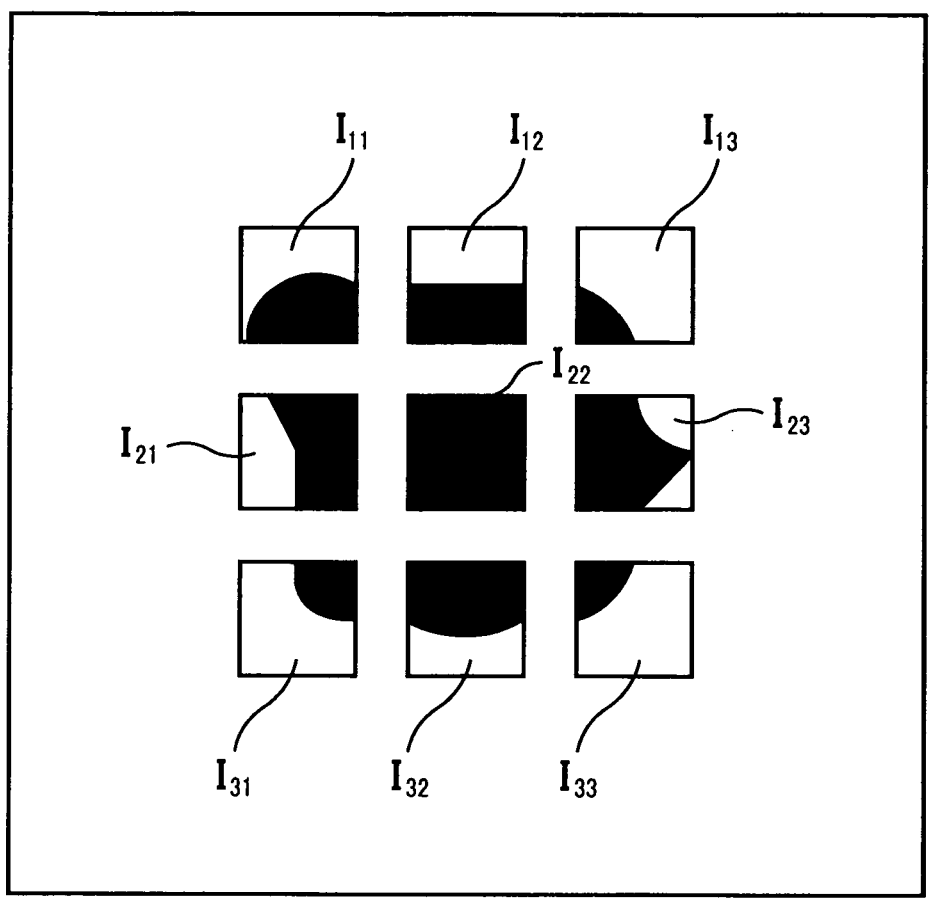
FIG. 10 is a diagram showing an example of a peripheral image obtained in the peripheral area of a micro observation point.

In this example, in order to make the description easy to understand, as shown in FIG. 10, nine images $I_{11}$ to $I_{33}$ are required in order to obtain an image of the whole range of the biological change region (the black region in FIG. 10), and the micro image obtained by the micro observation described above is described as a micro image $I_{22}$ in central part thereof.

At step S91, the observation unit 27 carries out micro observation of a micro observation point, similarly to step S40 in FIG. 6. In this example, a micro image $I_{22}$ shown in FIG. 10 is obtained by micro observation of the micro observation point.

At step S92, the image analysis unit 34 applies prescribed image analysis processing to the acquired micro image, for instance, and from this analysis result, it is judged whether or not it has been possible to acquire an image of the whole of the biological change region. In step S92, if it is judged that the whole of the biological change region is contained within the micro image, then it is not necessary to process the micro image, and therefore the procedure advances to step S41 in FIG. 6. The processing in this case is similar to the processing described in relation to FIG. 6 above.

On the other hand, if it is judged at step S92 that the whole of the biological change region is not contained within the micro image, then at step S93, the observation unit 27 carries out micro observation in the peripheral area of the micro observation point as well. By this micro observation, a peripheral image including the biological change region is obtained from the region of the peripheral area of the micro observation point. For example, as shown in FIG. 10, when a micro image $I_{22}$ has been obtained by micro observation of the micro observation point, then eight peripheral images $I_{11}$ to $I_{13}$, $I_{21}$, $I_{23}$, $I_{31}$ to $I_{33}$ are obtained by further micro observation of the peripheral area. In other words, if the one micro image $I_{22}$ and the eight peripheral images $I_{11}$ to $I_{13}$, $I_{21}$, $I_{23}$, $I_{31}$ to $I_{33}$, are viewed as a single image, then an image including the whole of the biological change region is obtained.

Thereupon, in step S94, it is judged whether or not to carry out tiling, and if tiling is not to be carried out, then processing advances to step S41 in FIG. 6, whereas if tiling is to be carried out, the processing advances to step S95.

At step S95, similarly to the tiling process in step S73 in FIG. 7, the image processing unit 58 generates one tiled image by tiling the micro image $I_{22}$ obtained by micro observation of the micro observation point, and the peripheral images $I_{11}$ to $I_{13}$, $I_{21}$, $I_{23}$, $I_{31}$ to $I_{33}$ obtained by micro observation of the peripheral area of the micro observation point. Since the tiled image is regarded as one micro image, then a micro image including the whole of the biological change region is produced. Thereupon, the processing advances to step S41 in FIG. 6 and biological change judgment processing is carried out.

In this way, if it is not possible for the whole range of a biological change region to be contained in one micro image, it is possible to acquire an image of the whole of the biological change region by acquiring and tiling peripheral images. By this means, it is possible to check the whole of the biological specimen which is an object of observation, and therefore it is possible to carry out accurate observation.

As described above, according to the present embodiment, change in the biological specimen which is the object of tracking by macro observation is extracted over a broad range, whereupon a biological change region identified by macro observation can be observed microscopically, and therefore it is possible to carry out observation accurately.

More specifically, in the present embodiment, it is possible to carry out time lapse observation of a region where an observation object has changed, at a higher magnification rate, and therefore it is possible to perform detailed observation. Furthermore, if the observation magnification rate is fixed in advance to a high magnification rate, then it is only possible to observe a limited narrow range, and there is a possibility that change in the observation object which is of interest to the user cannot be detected, but in the present invention, it is possible to detect change in the observation object over a broad range, and therefore the observation object can be observed reliably.

In the present embodiment, a biological specimen observation apparatus which performs cultivation and observation of biological specimens is described as an example, but the present invention can also be applied to an observation apparatus, such as a microscope, which carries out observation of biological specimens only. Furthermore, by introducing image analysis software according to the present embodiment, it is possible to discover stem cell colonies in a liver, for example. Subsequently, it is possible to extract only good stem cell colonies by micro image analysis of the stem cell colonies of the liver. Therefore, this is useful for hepatocellular management.

The series of processing described above can be executed by hardware or can be executed by software. If the series of process is executed by software, then a program which constitutes that software is installed from a storage medium to a computer equipped with dedicated hardware or a generic personal computer, for instance, which is capable of executing functions of various types by installing programs of various types.

This recording medium may be constituted by a magnetic disk, an optical disk, a magneto-optical disk or a semiconductor memory, or the like, on which a program is recorded and which is distributed in order to supply programs to a user, separately from a computer, or besides this, a ROM (Read Only Memory) or a HDD (Hard Disk Drive), or the like, which is presented to a user in a previously installed state in a computer.

Furthermore, a program which causes the series of processing described above to be executed may be installed in a computer via a wired or wireless communications medium such as a local area network, the Internet, or digital satellite communications, by means of an interface such as a router, modem, or the like, in accordance with requirements.

In the present specification, the steps which describe a program stored on a recording medium naturally include processing which is carried out in a time series according to the sequence in which it is listed, as well as processing which is carried out in parallel or independently, rather than being carried out in a time series.

Furthermore, the embodiment of the present invention is not limited to the embodiments described above and various modifications are possible within a range that does not deviate from the essence of the present invention.

EXPLANATION OF REFERENCE NUMERALS

1: biological specimen observation apparatus; 11: first frame; 12: second frame; 15: culture vessel; 21: thermostatic chamber; 22: front face door; 23: front face opening; 24: inward/outward conveyance port; 25: stocker; 26: vessel conveyance mechanism; 27: observation unit; 31: control unit; 32: display panel; 33: observation information memory unit; 34: image analysis unit; 35: observation control unit; 41: transmission light illumination unit; 42: epifluorescent illumination unit; 43: specimen platform; 44: observation unit; 51: transmission light LED; 52: transmission light optical system; 53a to 53c: fluorescence LED; 54: fluorescence optical system; 55: objective lens; 56: stage; 57: imaging unit; 58: image processing unit

The invention claimed is:

1. A biological specimen observation apparatus which observes temporal change in a biological specimen, comprising:
a first imaging device configured to acquire a fluorescent macro image by capturing an image of a macro region of a broad range of the biological specimen, while time lapse observation is performed;
a second imaging device configured to capture an image of a micro region of change in the biological specimen identified at a micro observation point, while the time lapse observation is performed; and
one or more processors configured to:
determine a location of a biological change region in the acquired macro image based on an image analysis of the macro image, the biological change region representing a region of change in the biological specimen, the image analysis including determining a change in a luminous point of the macro image during the time lapse observation, the biological change region being a region in which the change in the luminous point of the macro image has occurred;
register the micro observation point corresponding to the determined biological change region;
judge whether or not biological change has continued in the biological change region at the micro observation point, from the acquired micro image; and
update the registered micro observation point based on whether or not biological change has continued in the biological change region at the micro observation point.

2. The biological specimen observation apparatus according to claim 1, wherein the one or more processors are further configured to erase the registered micro observation point, when judgment is made that there is no continued biological change in the biological change region at the micro observation point.

3. The biological specimen observation apparatus according to claim 1, wherein the one or more processors are further configured to accept registration or change of the micro observation point.

4. The biological specimen observation apparatus according to claim 1, wherein the one or more processors are further configured to generate a tiled image by pasting together a plurality of captured images obtained by capturing images of the biological specimen, and to
extract the biological change region from the generated tiled image.

5. The biological specimen observation apparatus according to claim 1, wherein the one or more processors are further configured to generate a tiled image, when a whole range of the biological change region is not included in the acquired micro image, by acquiring a peripheral image obtained by capturing images of a peripheral area of the micro observation point and pasting together the acquired peripheral image and micro image.

6. A biological specimen observation apparatus which observes temporal change in a biological specimen, comprising:
a first imaging device configured to acquire a macro image by capturing a fluorescent image of a macro region of the biological specimen, while time lapse observation is executed;
a second imaging device configured to perform time lapse observation and to acquire micro images of the biological specimen at a micro observation point; and
one or more processors configured to identify the micro observation point where micro observation is to be performed in the macro region of the biological specimen, on the basis an image analysis of the macro images of a time series obtained by the first imaging device, the image analysis including determining a change in a luminous point of the macro images during the time lapse observation, the micro observation point being included in a biological change region in which the change in the luminous point of the macro images has occurred.

7. The biological specimen observation apparatus according to claim 6, wherein the one or more processors are further configured to:
switch between a macro observation priority mode which prioritizes macro observation by the first imaging device and a micro observation priority mode which prioritizes micro observation by the second imaging device; and
when there is overlap in an observation schedule of the macro observation and micro observation, implement control so that, first, acquisition of the macro image is carried out and immediately after completion of this acquisition, acquisition of the micro image is carried out when the macro observation priority mode has been selected, and implement control so that, first, acquisition of the micro image is carried out and immediately after completion of this acquisition, acquisition of the macro image is carried out when the micro observation priority mode has been selected.

8. A biological specimen observation apparatus which observes temporal change in a biological specimen, comprising:
a first imaging device configured to acquire a fluorescent macro image by capturing an image of a macro region of a broad range of the biological specimen, while time lapse observation is performed;
a second imaging device configured to acquire a micro image by capturing an image of a micro region in the macro region of the biological specimen, while time lapse observation is performed; and
one or more processors configured to analyze temporal change in the biological specimen from the acquired macro image and the acquired micro image by determining a location of a biological change region in the acquired macro image based on an image analysis of the macro image, the biological change region representing a region of change in the biological specimen, the image analysis including determining a change in a luminous point of the macro image during the time lapse observation, the biological change region being a region in which the change in the luminous point of the macro image has occurred.

9. The biological specimen observation apparatus according to claim 1, wherein determining the change in the luminous point of the macro image during the time lapse observation includes determining a change in a value of one or more pixels of the macro image during the time lapse observation.

10. The biological specimen observation apparatus according to claim 1, wherein the one or more processors are further configured to:
- determine whether the biological change region is a newly extracted biological change region or an already registered biological change region;
- when the biological change region is a newly extracted biological change region, newly register the micro observation point corresponding to the newly extracted biological change region as central coordinates of the newly extracted biological change region; and
- when the biological change region is an already registered biological change region, update the micro observation point corresponding to the biological change region.

\* \* \* \* \*

UNITED STATES PATENT AND TRADEMARK OFFICE
CERTIFICATE OF CORRECTION

PATENT NO. : 9,442,282 B2
APPLICATION NO. : 13/251673
DATED : September 13, 2016
INVENTOR(S) : Hideo Kuroda et al.

Page 1 of 1

It is certified that error appears in the above-identified patent and that said Letters Patent is hereby corrected as shown below:

In the Claims,

Column 16, Line 22, Claim 6:

After "basis" insert --of--, therefor.

Signed and Sealed this
Twenty-ninth Day of November, 2016

Michelle K. Lee
*Director of the United States Patent and Trademark Office*